(12) United States Patent
Brizzi et al.

(10) Patent No.: US 11,464,799 B2
(45) Date of Patent: Oct. 11, 2022

(54) COMPOSITION OF EXTRACELLULAR VESICLES (EVS) AND MEDICAL USES THEREOF

(71) Applicant: UNICYTE EV AG, Oberdorf (CH)

(72) Inventors: Maria Felice Brizzi, Turin (IT); Giovanni Camussi, Turin (IT); Andrea Ranghino, Turin (IT)

(73) Assignee: USICYTE EV AG, Oberdorf (CH)

( * ) Notice: Subject to any disclaimer, the term of this patent is extended or adjusted under 35 U.S.C. 154(b) by 508 days.

(21) Appl. No.: 16/341,319

(22) PCT Filed: Oct. 11, 2017

(86) PCT No.: PCT/EP2017/075966
§ 371 (c)(1),
(2) Date: Apr. 11, 2019

(87) PCT Pub. No.: WO2018/069408
PCT Pub. Date: Apr. 19, 2018

(65) Prior Publication Data
US 2019/0381095 A1 Dec. 19, 2019

(30) Foreign Application Priority Data
Oct. 12, 2016 (EP) .................................... 16193502

(51) Int. Cl.
| | | |
|---|---|---|
| *C12N 5/078* | (2010.01) | |
| *G01N 33/50* | (2006.01) | |
| *A61P 9/10* | (2006.01) | |
| *A61K 35/12* | (2015.01) | |
| *A61K 35/14* | (2015.01) | |
| *A61P 17/02* | (2006.01) | |
| *A61K 9/127* | (2006.01) | |
| *A61K 35/16* | (2015.01) | |

(52) U.S. Cl.
CPC ............ *A61K 35/14* (2013.01); *A61K 9/1271* (2013.01); *A61K 35/12* (2013.01); *A61K 35/16* (2013.01); *A61P 9/10* (2018.01); *A61P 17/02* (2018.01); *C12N 5/0634* (2013.01); *G01N 33/5005* (2013.01); *C12N 2502/00* (2013.01)

(58) Field of Classification Search
None
See application file for complete search history.

(56) References Cited

U.S. PATENT DOCUMENTS

2015/0190429 A1 7/2015 Beelen et al.

FOREIGN PATENT DOCUMENTS

| EP | 2450032 | 5/2012 |
|---|---|---|
| WO | WO 2009/105044 | 8/2009 |
| WO | WO 213/025042 | 2/2013 |
| WO | WO 2013/158203 | 10/2013 |
| WO | WO 2016/156865 | 10/2016 |

OTHER PUBLICATIONS

Schagat T, Paguio A, Kopish K. Normalizing genetic reporter assays approaches and considerations for increasing consistency and statistical significance. Cell Notes. 2007;17: 9-12 (Year: 2007).*
Improved outcomes software. "Normalization overview." (2008) http://www.improvedoutcomes.com/docs/WebSiteDocs/PreProcessing/Normalization/Normalization_Overview.htm (Year: 2008).*
Batrakova EV, Kim MS. Development and regulation of exosome-based therapy products. Wiley Interdiscip Rev Nanomed Nanobiotechnol. Sep. 2016;8(5):744-57. (Year: 2016).*
Fendl et al. Characterization of extracellular vesicles in whole blood: Influence of pre-analytical parameters and visualization of vesicle-cell interactions using imaging flow cytometry. Biochemical and Biophysical Research Communications. vol. 478, No. 1, Jul. 19, 2016.
Anonymous ed. System Biosciences: Exosome Research: One-step Exosome isolation from Serum, ExoQuick Benefits. Exosome Research, Jan. 1, 2013, pp. 1-7.
Inal et al. Blood/plasma secretome and microvesicles. BioChimica et Biophysica ACTA—Proteins & Proteomics, vol. 1834, No. 11, Jan. 1, 2013, pp. 2317-2325.
Samir et al. Extracellular vesicles: biology and emerging therapeutic opportunities. Nature Review Drug Discovery, vol. 12, Apr. 15, 2013, p. 347-357.
Vega-Avila et al. An overview of colorimetric assay methods used to assess survival or proliferation of mammalian cells. Proceedings of the Western Pharmacology Society 2011, vol. 54, 2011, pp. 10-14.
Doeppner et al. Extracellular vesicles improve post-stroke neuroregneration and prevent postischemic immunosuppression. Stem Cells Translational Medicine, vo. 4, No. 10, Oct. 1, 2015, pp. 1131-1143.
Kholia et al. Extracellular vesicles as new players in angiogenesis. Vascular Pharmacology, 86 (2016) 64-70.
Koniusz et al. Extracellular vesicles in Physiology, Pathology, and Therapy of the Immune and Central Nervous System, with focus n Extracellular Vesicles derived from Mesenchymal stem cells as therapeutic tools. Frontiers in Cellular Neuroscience, May 2016, vol. 10, article 109, pp. 1-20.
Nolte et al. Standardized assessment of cell proliferation: The approach of the RITA-CEP A working group, Experimental and Toxicologoc Pathology, 57 (2005) 91-103.
Sieveking et al. Strikingly Different Angiogenic Properties of Endothellal Progenitor Cell Subpopulations. Journal of the American College of Cardiology, vol. 51, No. 6, 2008.

(Continued)

*Primary Examiner* — Daniel C Gamett
(74) *Attorney, Agent, or Firm* — Jacobson Holman PLLC

(57) ABSTRACT

The present invention relates to compositions of extracellular vesicles (EVs) which are characterized by a strong proangiogenic activity and are effective in the therapeutic treatment of ischemic diseases and ischemic injuries or in wound healing. The extracellular vesicles (EVs) suitable for use in the compositions of the invention are either derived from a blood component or are selected by means of a potency test for pro-angiogenesis. Also disclosed is a method of manufacturing a pharmaceutical preparation of extracellular vesicles (EVs) characterized by a strong proangiogenic activity.

5 Claims, 11 Drawing Sheets

(56) References Cited

OTHER PUBLICATIONS

Roposo et al. Extracellular vesicles: Exosomes, microvesicles, and friends. J. Cell Bio. vol. 200, No. 4, 373-383.

Lee et al. Isolation of mutipotent mesenchymal stem cells from umbilical cord blood, Blood, vol. 103, No. 5. Mar. 1, 2004, pp. 1669-1675.

Caporali et al.MicroRNAs in Postischemic Vascular Repair. Cardiology Research and Practice, vol. 2012, article ID 486702, 7 pages.

Lopatina et al. Platelet-derived growth factor regulates the secretion of extracellular vesicles by adipose mesenchymal stem cells and enhances their angiogenic potential. Cell Communcation and Signaling 2014, 12:26, pp. 1-12.

* cited by examiner

| Serum EV | | |
|---|---|---|
| | MARKERS | % |
| *Monocyte/ Leucocytes* | CD14 | 8,6±0,7 |
| | CD15 | 7,8±0,9 |
| | CD45 | 4,5±0,3 |
| *Adhesion* | ALPHA6 | 11,3±1,1 |
| | CD44 | 11,10±1,2 |
| | CD29 | 16,5±1,1 |
| *Endothelial* | CD31 | 27,1±2,4 |
| | KDR | 11,5±0,9 |
| *Platelet* | CD62P | 20,1±2,2 |
| | P SEL | 28,8±3,1 |
| | CD42B | 10,4±1,4 |

Fig.1

| | | | |
|---|---|---|---|
| sEV 1 | 42,8 | 62,5 | 52,65 |
| sEV 2 | 54,4 | 56,4 | 55,4 |
| sEV 3 | 31,9 | 89,5 | 60,7 |
| sEV 4 | 53,3 | 64,1 | 58,7 |
| sEV 5 | 68,7 | 55,5 | 62,1 |
| sEV 6 | 43,8 | 77,6 | 60,7 |
| sEV 7 | 88,5 | 66,2 | 77,4 |
| sEV 8 | 65,5 | 44,4 | 54,95 |
| sEV 9 | 56,5 | 50,1 | 53,3 |
| sEV 10 | 31,5 | 99,8 | 65,7 |
| sEV 11 | 54,5 | 0 | 27,3 |
| sEV 12 | 99,2 | 32,2 | 65,7 |
| sEV 13 | 28,8 | 24,5 | 26,7 |
| sEV 14 | 41,7 | 68,6 | 55,2 |
| sEV 15 | 50 | 55 | 52,5 |
| sEV 16 | 8,3 | 19,1 | 13,7 |
| sEV 17 | 66,7 | 41,1 | 53,9 |
| sEV 18 | 79,16 | 0,85 | 40 | sEVs enhance blood perfusion in an ischemic hindlimb model sEVs increase capillary density in ischemic hindlimb sEVs protect muscles from ischemia-induced damage

Comparison of miR expression between ineffective and effective sEVs

| Gene symbol | sEV treatment (fold change) | | | Gene symbol | sEV treatment (fold change) | | |
|---|---|---|---|---|---|---|---|
| Upregulated genes | | | | Downregulated genes | | | |
| PTGS1 | 8,512 | ± | 1,45 | FIGF | 0,008 | ± | 0,09 |
| ID1 | 4,941 | ± | 0,28 | TGFBR1 | 0,123 | ± | 0,59 |
| THBS1 | 4,728 | ± | 0,55 | HPSE | 0,142 | ± | 0,09 |
| SERPINE1 | 4,446 | ± | 1,28 | TIMP3 | 0,176 | ± | 0,88 |
| FN1 | 4,212 | ± | 1,38 | IL8 | 0,333 | ± | 0,65 |
| SERPINF1 | 3,527 | ± | 1,22 | TGFB2 | 0,404 | ± | 0,82 |
| ERBB2 | 3,223 | ± | 1,27 | CXCL1 | 0,426 | ± | 0,72 |
| TIE1 | 3,090 | ± | 0,99 | ANGPT1 | 0,446 | ± | 0,54 |
| IFNG | 3,089 | ± | 0,47 | HGF | 0,459 | ± | 0,85 |
| CXCL9 | 3,065 | ± | 1,53 | ANGPTL4 | 0,484 | ± | 0,15 |
| TGFB1 | 2,792 | ± | 0,49 | FGFR3 | 0,663 | ± | 0,37 |
| THBS2 | 2,675 | ± | 0,07 | CXCL10 | 0,776 | ± | 0,71 |
| KDR | 2,524 | ± | 1,57 | SPHK1 | 0,976 | ± | 0,16 |
| PECAM1 | 2,499 | ± | 0,34 | PF4 | 1,051 | ± | 0,63 |
| PROK2 | 2,476 | ± | 1,68 | IGF1 | 1,105 | ± | 0,58 |
| MMP14 | 2,346 | ± | 0,95 | F3 | 1,137 | ± | 0,62 |
| COL4A3 | 2,339 | ± | 1,99 | COL18A1 | 1,574 | ± | 0,84 |
| ANPEP | 2,315 | ± | 1,96 | TNF | 3,717 | ± | 0,30 |
| TIMP1 | 2,239 | ± | 0,30 | CXCL6 | 5,803 | ± | 0,08 |
| ENG | 2,186 | ± | 0,58 | BAI1 | 19,833 | ± | 0,45 |
| MMP9 | 2,118 | ± | 0,23 | TYMP | 26,027 | ± | 0,01 |
| IL1B | 1,899 | ± | 1,04 | | | | |
| NOS3 | 1,851 | ± | 2,42 | | | | |
| HIF1A | 1,571 | ± | 1,12 | | | | |
| NRP1 | 1,490 | ± | 0,53 | | | | |
| CCL11 | 1,447 | ± | 0,36 | | | | |
| EFNA1 | 1,332 | ± | 0,65 | | | | |
| EFNB2 | 1,296 | ± | 1,40 | | | | |
| CTGF | 1,202 | ± | 0,15 | | | | |
| S1PR1 | 1,159 | ± | 0,29 | | | | |
| CCL2 | 1,123 | ± | 0,62 | | | | |
| NRP2 | 1,117 | ± | 0,07 | | | | |
| MMP2 | 1,093 | ± | 0,04 | | | | |
| PGF | 1,046 | ± | 0,41 | | | | |
| FLT1 | 1,014 | ± | 1,84 | | | | |
| IFNA1 | 0,958 | ± | 0,48 | | | | |
| ITGB3 | 0,919 | ± | 1,18 | | | | |
| EPHB4 | 0,827 | ± | 0,17 | | | | |
| TIMP2 | 0,731 | ± | 1,49 | | | | |
| VEGFB | 0,720 | ± | 1,45 | | | | |
| AKT1 | 0,712 | ± | 0,90 | | | | |
| CDH5 | 0,677 | ± | 0,87 | | | | |
| ITGAV | 0,637 | ± | 1,97 | | | | |
| VEGFA | 0,617 | ± | 0,61 | | | | |
| NOTCH4 | 0,612 | ± | 2,04 | | | | |
| MDK | 0,533 | ± | 2,03 | | | | |
| FGF2 | 0,414 | ± | 0,44 | | | | |
| ANGPT2 | 0,414 | ± | 0,72 | | | | |
| PLAU | 0,391 | ± | 0,14 | | | | |
| PLG | 0,384 | ± | 0,93 | | | | |
| IL6 | 0,367 | ± | 0,49 | | | | |
| JAG1 | 0,263 | ± | 0,79 | | | | |
| CXCL5 | 0,262 | ± | 0,58 | | | | |
| LEP | 0,213 | ± | 0,02 | | | | |
| TGFA | 0,212 | ± | 0,70 | | | | |
| FGF1 | 0,199 | ± | 0,69 | | | | |
| ANG | 0,174 | ± | 0,43 | | | | |
| EGF | 0,173 | ± | 0,56 | | | | |
| PDGFA | 0,158 | ± | 0,31 | | | | |
| EDN1 | 0,142 | ± | 0,27 | | | | |
| VEGFC | 0,127 | ± | 0,93 | | | | |
| LECT1 | 0,063 | ± | 0,28 | | | | |
| TEK | 0,061 | ± | 0,15 | | | | |

Fig.11

| Gene symbol | VEGF (fold change) | | Gene symbol | VEGF (fold change) | |
|---|---|---|---|---|---|
| Upregulated genes | | | Downregulated genes | | |
| IL6 | 3,380 | ± 1,32 | AKT1 | 0,015 | ± 0,02 |
| VEGFA | 3,356 | ± 0,54 | FIGF | 0,142 | ± 0,13 |
| VEGFC | 3,329 | ± 0,10 | CDH5 | 0,168 | ± 0,28 |
| PTGS1 | 3,304 | ± 0,34 | COL18A1 | 0,205 | ± 1,61 |
| PGF | 3,214 | ± 0,10 | ANG | 0,206 | ± 0,45 |
| TIE1 | 3,122 | ± 0,28 | IL8 | 0,232 | ± 0,11 |
| PECAM1 | 3,076 | ± 0,25 | TGFB1 | 0,311 | ± 0,10 |
| ID1 | 3,065 | ± 0,29 | LEP | 0,332 | ± 0,57 |
| JAG1 | 3,040 | ± 2,32 | TGFA | 0,368 | ± 0,66 |
| NOS3 | 3,012 | ± 0,54 | CXCL1 | 0,438 | ± 0,59 |
| ITGB3 | 2,825 | ± 1,44 | TGFB2 | 0,470 | ± 0,04 |
| THBS1 | 1,773 | ± 1,02 | IL1B | 0,550 | ± 0,30 |
| ERBB2 | 1,621 | ± 0,35 | SPHK1 | 0,561 | ± 0,23 |
| FN1 | 1,559 | ± 0,54 | TEK | 0,652 | ± 0,13 |
| CTGF | 1,375 | ± 1,72 | ENG | 0,686 | ± 1,95 |
| NRP1 | 1,305 | ± 1,04 | TIMP3 | 0,738 | ± 0,70 |
| ANPEP | 1,296 | ± 1,53 | VEGFB | 0,747 | ± 0,69 |
| HIF1A | 1,284 | ± 0,29 | IGF1 | 0,770 | ± 0,51 |
| TIMP2 | 1,237 | ± 1,48 | TNF | 0,874 | ± 0,75 |
| NRP2 | 1,228 | ± 1,22 | PLG | 0,990 | ± 0,25 |
| HPSE | 1,216 | ± 1,73 | ANGPTL4 | 0,996 | ± 0,23 |
| EFNA1 | 1,184 | ± 0,24 | CXCL10 | 1,183 | ± 0,00 |
| PLAU | 1,154 | ± 1,71 | CXCL5 | 1,608 | ± 0,54 |
| F3 | 1,124 | ± 0,96 | CXCL6 | 1,809 | ± 0,12 |
| FGF2 | 1,116 | ± 0,31 | TYMP | 2,221 | ± 0,44 |
| S1PR1 | 0,950 | ± 1,42 | ANGPT1 | 2,478 | ± 0,41 |
| SERPINE1 | 0,915 | ± 1,64 | CXCL9 | 2,891 | ± 0,23 |
| COL4A3 | 0,872 | ± 0,26 | CCL11 | 4,025 | ± 0,28 |
| EDN1 | 0,851 | ± 0,43 | THBS2 | 4,376 | ± 0,23 |
| ITGAV | 0,830 | ± 0,01 | LECT1 | 6,576 | ± 0,19 |
| CCL2 | 0,753 | ± 1,33 | BAI1 | 7,000 | ± 1,27 |
| SERPINF1 | 0,682 | ± 1,60 | MMP9 | 7,850 | ± 0,16 |
| EPHB4 | 0,633 | ± 1,07 | FGFR3 | 9,000 | ± 0,23 |
| TIMP1 | 0,629 | ± 0,43 | IFNG | 9,256 | ± 0,14 |
| FLT1 | 0,587 | ± 0,64 | HGF | 14,873 | ± 0,09 |
| EFNB2 | 0,555 | ± 1,68 | EGF | 16,857 | ± 0,01 |
| MMP2 | 0,497 | ± 0,38 | | | |
| FGF1 | 0,457 | ± 1,72 | | | |
| ANGPT2 | 0,440 | ± 0,09 | | | |
| KDR | 0,417 | ± 1,19 | | | |
| TGFBR1 | 0,416 | ± 0,32 | | | |
| MMP14 | 0,415 | ± 0,00 | | | |
| PF4 | 0,342 | ± 0,83 | | | |
| IFNA1 | 0,300 | ± 0,69 | | | |
| MDK | 0,243 | ± 1,31 | | | |
| PDGFA | 0,205 | ± 0,24 | | | |
| NOTCH4 | 0,186 | ± 1,68 | | | |
| PROK2 | 0,057 | ± 0,60 | | | |

Fig.12

| Category | Term | Count | % | PValue | Genes | Fold Enrichment | Bonferroni | Benjamini |
|---|---|---|---|---|---|---|---|---|
| KEGG_PATHWAY | hsa04350:TGF-beta signaling pathway | 3 | 30 | 0.004747 | ID1, IFNG, THBS1 | 22 | 0.1939276 | 0.193928 |
| KEGG_PATHWAY | hsa04510:Focal adhesion | 3 | 30 | 0.028635 | ERBB2, THBS1, FN1 | 9 | 0.5693818 | 0.343785 |
| KEGG_PATHWAY | hsa05219:Bladder cancer | 2 | 20 | 0.056437 | ERBB2, THBS1 | 30 | 0.814492 | 0.429677 |
| KEGG_PATHWAY | hsa04115:p53 signaling pathway | 2 | 20 | 0.089987 | SERPINE1, THBS1 | 19 | 0.9350794 | 0.495228 |

COMPOSITION OF EXTRACELLULAR VESICLES (EVS) AND MEDICAL USES THEREOF

The present invention relates to new therapeutic applications of extracellular vesicle preparations (EVs), in particular in the therapeutic treatment of ischemic diseases, ischemic injuries and in wound healing. A focus lies on the treatment of vascular ischemic diseases or injuries such as acute myocardial infarction, acute cerebrovascular disease, acute and chronic peripheral artery disease or acute kidney ischemia.

Peripheral arterial disease (PAD) is a widespread condition caused by atherosclerosis of the peripheral arteries. Although surgical or endovascular intervention remains the standard therapy to improve blood flow, even after successful revascularisation, most patients complain of persistent or recurring symptoms. This implies that new therapeutic options for PAD still represent a major unmet need.

The formation of newly born capillary blood vessels, neovascularization, is a crucial event in rescuing tissue after ischemia. A vast array of pre-clinical and clinical data indicates that stem cells can contribute to the healing processes by improving vascularization. Additionally, the transient detection of stem cells into site of tissue damage has suggested that paracrine mechanisms could mainly contribute to stem cell actions. Among such paracrine mechanisms "exosomes", vesicles derived from the endosomal membrane compartment by exocytosis, and "ectosomes/microvesicles", vesicles generated by the budding of cell plasma membranes are included. Due to the overlap in characteristics and biological activities of exosomes and ectosomes/microvesicles, recently the more inclusive term "extracellular vesicles" (EVs) was suggested. EVs re powerful cell-to-cell communication vehicles both in physiological and pathological conditions. Recent studies provide evidences that transfer of EV cargo can dictate recipient cell fate. Indeed, the transfer of EVs cargo, including nucleic acids and proteins, into recipient cells represents the most relevant mechanism of their actions.

So far, the most studied EVs are those released by stem cells, because of their ability to mimic the effects of their cell of origin. Depending on the pathological settings, different phenotypic changes have been described in target cells. In order to try to characterize the mechanism of action of stem cell-derived EVs, transcriptomic and proteomic analysis has been performed. In particular, a robust pro-angiogenic profile has been described in EVs recovered from mesenchymal stem cells derived from bone marrow or adipose tissues. This has suggested the potential impact of these EVs in clinical settings, including ischemic-related diseases.

However, the use of stem cell-derived EVs has the drawback that isolation of such EVs requires in vitro culturing of huge amounts of stem cells in order to obtain a useful number of EVs to be employed.

In order to overcome these and other drawbacks of the prior art, the present inventors studied blood and blood fractions such as serum and plasma as potential sources for EVs. In fact, EVs released within a defined microenvironment can act locally (paracrine action) or they may even act at a distance from the cell of origin (endocrine action). The endocrine action mainly relies on the circulation of EVs in peripheral fluids. This implies that blood could be the natural milieu used by EVs to gain access to their targets. Moreover, EVs can be secreted by all blood cells and retrieved in blood fluids, in which their functions however remain mostly unknown.

As it will be illustrated in detail in the following examples, with their studies the inventors found that EVs derived from a blood component possess a strong proangiogenic activity as measured in a potency test in which vascular endothelial growth factor (VEGF) is used as the reference pro-angiogenic growth factor, whereby EVs derived from a blood component are particularly effective in the therapeutic treatment of ischemic diseases and ischemic injuries or in wound healing.

Therefore, a first aspect of the present invention is a composition of extracellular vesicles (EVs) isolated from a blood component for use in the treatment of an ischemic disease or ischemic injury or in wound healing by proangiogenic therapy. In the present description, the extracellular vesicles isolated from a blood component shall be designated in short as "sEVs".

The ischemic disease or ischemic injury treated with the EVs composition according to the present invention is preferably a vascular disease or injury. Even more preferably, it is selected from the group consisting of acute myocardial infarction, acute cerebrovascular disease, acute and chronic peripheral artery disease or acute kidney ischemia.

The blood component from which the sEVs for use according to the present invention are isolated is preferably blood, serum or plasma. More preferably, the sEVs are prepared from a blood donation of a healthy donor.

In all of the above-described embodiments, it is preferred that the composition for use according to present invention be a bulk preparation essentially capturing all EVs present in blood, serum, plasma or in the conditioned medium based on size exclusion.

In all of the above-described embodiments, it is also preferred that the EVs are derived from human cells.

Furthermore, in all of the above-described embodiments, the composition may be a pharmaceutical preparation, which includes EVs as defined above as well as a pharmaceutically acceptable carrier, vehicle or diluent. The selection of the carrier, vehicle or diluent as well as of any other excipient required for the preparation of the desired pharmaceutical dosage form falls within the ability of the person skilled in the art.

The person skilled in the art is also able to identify the EVs dose required, which mainly depends on the condition to be treated and the patient's characteristics. In general, a therapeutically effective dose of EVs usually falls within the range of from $1\times10^{11}$ to $5\times10^{12}$ EVs/kg of body weight of the subject to be treated. The EVs composition according to the invention may be prepared in any suitable pharmaceutical dosage form.

As mentioned above, the inventors found that EVs isolated from a blood component possess a strong pro-angiogenic activity, which makes them particularly effective in the treatment of ischemic diseases and ischemic injuries or in wound healing.

It is envisaged that any composition comprising EVs possessing a pro-angiogenic activity comparable to that of the composition according to the first aspect of the invention, which comprises EVs isolated from a blood component, shall be equally or at least comparably effective in the treatment of ischemic diseases and ischemic injuries and in wound healing, irrespective of the source from which the EVs are prepared.

The pro-angiogenic activity of a composition of EVs from any source may be quantified by means of a potency test, which includes testing the EVs activity by means of a BrdU cell proliferation assay, or a tubulogenesis in vitro assay or both a BrdU cell proliferation assay and a tubulogenesis in vitro assay. In all of these embodiments, the BrdU cell proliferation assay and/or the tubulogenesis in vitro assay involve the use of a positive control and a negative control. In both methods, the basic growth medium is preferably endothelial basal medium.

The BrdU assay preferably uses HMEC cells seeded in matrigel. In the BrdU cell proliferation assay, serum (preferably 10% serum) is added in the positive control. The negative control is the same medium as the positive control but without the addition of serum. The BrdU assay is preferably based on a concentration of 10000 EVs per target cell.

The tubulogenesis in vitro assay preferably uses HUVEC cells. In the tubulogenesis in vitro assay, VEGF, preferably 10 ng/ml VEGF, is added to the positive control. The negative control is the same medium as the positive control but without VEGF addition. The tubulogenesis in vitro assay is preferably based on a concentration of 50000 EVs per target cell.

If the EVs measured activity exceeds a predetermined percentage of the positive control measured activity, for example >50% of the positive control measured activity, the EVs preparation tested is considered as active.

The potency tests relevant to identify compositions according to the invention are further detailed in the following description of the experimentations performed by the inventors, in particular in paragraphs 1.4.1 and 1.4.2 of the examples herein.

A second aspect of the present invention is a composition comprising EVs for use in the treatment of a disease or injury positively influenced by proangiogenic therapy or for use in wound healing, wherein the composition has a % activity of at least 50% when measured in a potency test which comprises the following steps:

measuring the activity of the composition by a BrdU cell proliferation assay;
measuring the activity of a negative control by a BrdU cell proliferation assay;
measuring the activity of a positive control by a BrdU cell proliferation assay;
calculating the % activity of the composition in the BrdU cell proliferation assay by applying the following formula:

$$\% \text{ activity} = \frac{\text{composition value} - \text{negative control value}}{\text{positive } crtl \text{ value} - \text{negative control value}} \times 100.$$

An alternative embodiment of this aspect of the invention is a composition of extracellular vesicles (EVs) for use in the treatment of a disease or injury positively influenced by proangiogenic therapy or for use in wound healing, wherein the composition has a % activity of at least 50% when measured in a potency test which comprises the following steps:

measuring the activity of the composition by a tubulogenesis assay;
measuring the activity of a negative control by a tubulogenesis assay;
measuring the activity of a positive control by a tubulogenesis assay;
calculating the % activity of the composition in the tubulogenesis assay by applying the following formula:

$$\% \text{ activity} = \frac{\text{composition value} - \text{negative control value}}{\text{positive } crtl \text{ value} - \text{negative control value}} \times 100.$$

In a further preferred embodiment, both the BrdU cell proliferation assay and the tubulogenesis in vitro assay are used for testing the activity of a given EVs composition against the activity of a positive control, in which case the average % activity values from the BrdU cell proliferation assay and the tubulogenesis assay are compared.

Due to its ability to enhance proliferation of cultured cells, as measured by the BrdU assay, the composition of EVs according to any of the disclosed embodiments is suitable for use as an additive to a culture medium for enhancing proliferation of cultured cells.

Furthermore, the above-described potency test is suitable to screen for EVs isolated from multiple preparations of body fluid or from the conditioned medium of a cell culture and to identify the pro-angiogenically active preparations for further processing.

Accordingly, a third aspect of the present invention is a method of manufacturing a pharmaceutical preparation of extracellular vesicles (EVs), comprising the steps of:

isolating EVs from multiple preparations of a body fluid or from the conditioned medium of a cell culture;
preparing one or more samples from the isolated EVs at a predetermined concentration of EVs;
testing the activity of each EVs sample in a potency test;
selecting for further processing to a pharmaceutical preparation the samples which exceed a predetermined activity; and optionally
pooling two or more of the active EVs samples.

The experimental results illustrated herein below show that EVs derived from serum or other blood components of healthy donors are able to induce proangiogenic signals in vitro and in vivo and that this effect is not lost even when sEV are pooled. sEVs also improve reperfusion in an in vivo preclinical model of PAD.

Transcriptomic and proteomic analysis revealed that TGFb1 and angiostatin are the most relevant mRNA and proteins carried by the sEVs derived from serum or other blood component. Based on this experimental finding, a composition comprising TGFb1 and angiostatin as the active ingredients is envisaged to exert the same or similar proangiogenic activity as the EVs used in the present invention.

Accordingly, the present invention also relates to a composition comprising extracellular vesicles (EVs) which carry transforming growth factor beta 1 (TGFb1), a nucleic acid coding for TGFb1 or an agent inducing TGFb1 expression and extracellular vesicles (EVs) which carry angiostatin or an agent capable of inducing angiostatin release, for use in the treatment of an ischemic disease or ischemic injury or in wound healing by proangiogenic therapy.

By way of example but without limitation, an agent capable of inducing the expression of TGFb1 is e.g. TGFb, ID1, IFNG, THBS1, SERPINE1, hsa-miR-17-5, hsa-miR-21 or hsa-miR-24; an agent capable of inducing angiostatin release is e.g. a metalloprotease, elastase, prostate-specific antigen (PSA), 13 KD serine protease or 24KD endopeptidase EVs carrying transforming growth factor beta 1 (TGFb1) or a nucleic acid coding for TGFb1 or an agent inducing TGFb1 expression and EVs carrying angiostatin or an agent capable of inducing angiostatin release may either be isolated by a suitable natural source or may be engineered to comprise the desired combination of active ingredients.

The above-defined composition of the invention is preferably a pharmaceutical composition. In addition to the above-mentioned active ingredients, the pharmaceutical composition further comprises a pharmaceutically acceptable excipient and/or carrier and/or diluent, which are selected by the person skilled in the art taking into account, inter alia, the selected pharmaceutical dosage form, administration route and administration regimen, as well as the patient's characteristics and the disease to be treated.

The invention will be better understood from the following examples which are provided by way of illustration only and which make reference to the appended drawings, wherein:

FIG. 1 is a table showing the FACS analysis results of sEVs performed with Guava Flow Cytometer. % values of surface antigens expression of different cell populations. The analysis showed that EVs from serum were a heterogeneous collection coming from different blood cell populations. % expressed as mean value±SD.

FIG. 2A relates to the sEV number distribution (18 healthy subjects) analyzed by Nanosight LM10 system. sEV mean particle concentration recovered from healthy donor bags correspond to $6,16\times10^8$ particles/ml.

FIG. 2B shows the Nanosight analysis results. sEV diameters were approximately 210 nm with a modal particle size of 183 nm.

FIG. 2C shows that starting from 2×10" of total particles, sEV RNA and protein recovery was similar in all samples analyzed (n=18), ranging from 300 to 500 ng (RNA) and about 1 µg (proteins). Data are expressed as mean±SD. #,*p value<0.05.

Figure 4A:
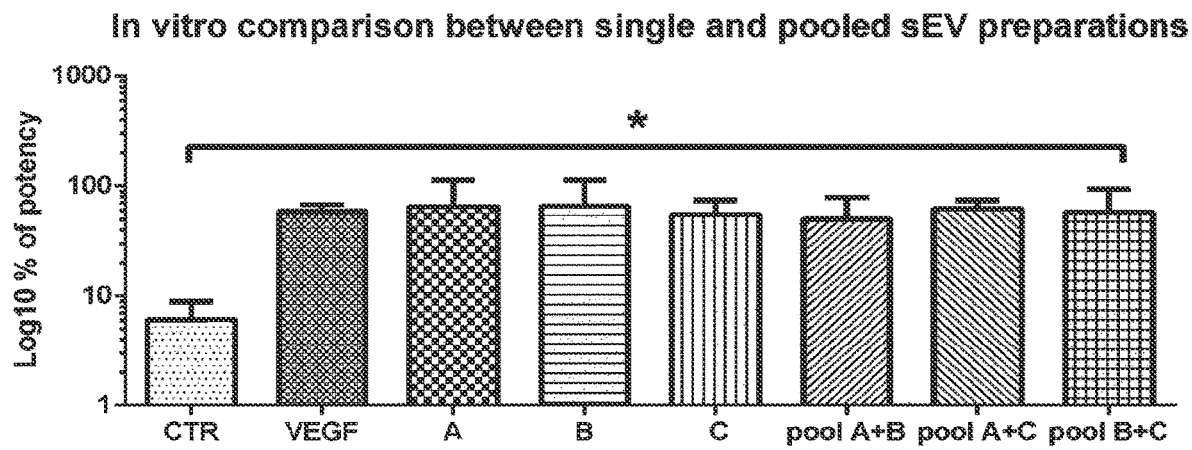
FIG. 4A shows the in vitro comparison between single and pooled EVs preparations. sEVs sharing comparative pro-angiogenic activities were pooled and analyzed for their biological activities. Pooled sEVs showed comparable biological effects with respect to single sEV preparations.
Figure 4B:
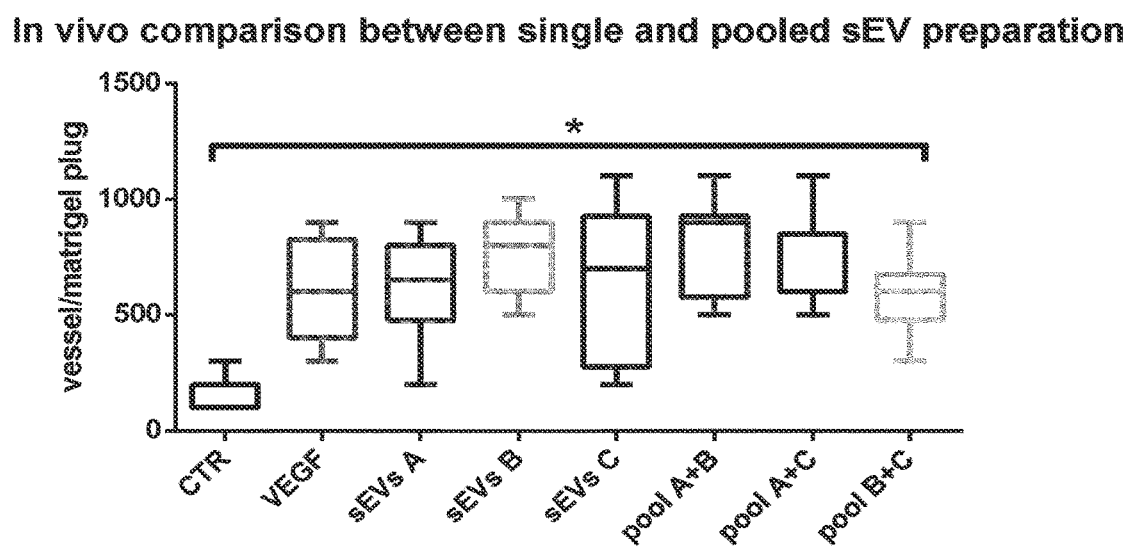

FIG. 4B shows the in vivo comparison between single and pooled EVs preparations. In vivo experiments were performed using an in vivo SCID mouse model. ECs were treated with sEV ($5\times10^4$ sEV/cell), mixed with Matrigel and injected subcutaneously into SCID mice. sEVs display in vivo proangiogenic activities. Similar effects were detected when pooled sEVs were analyzed.

Figure 5:
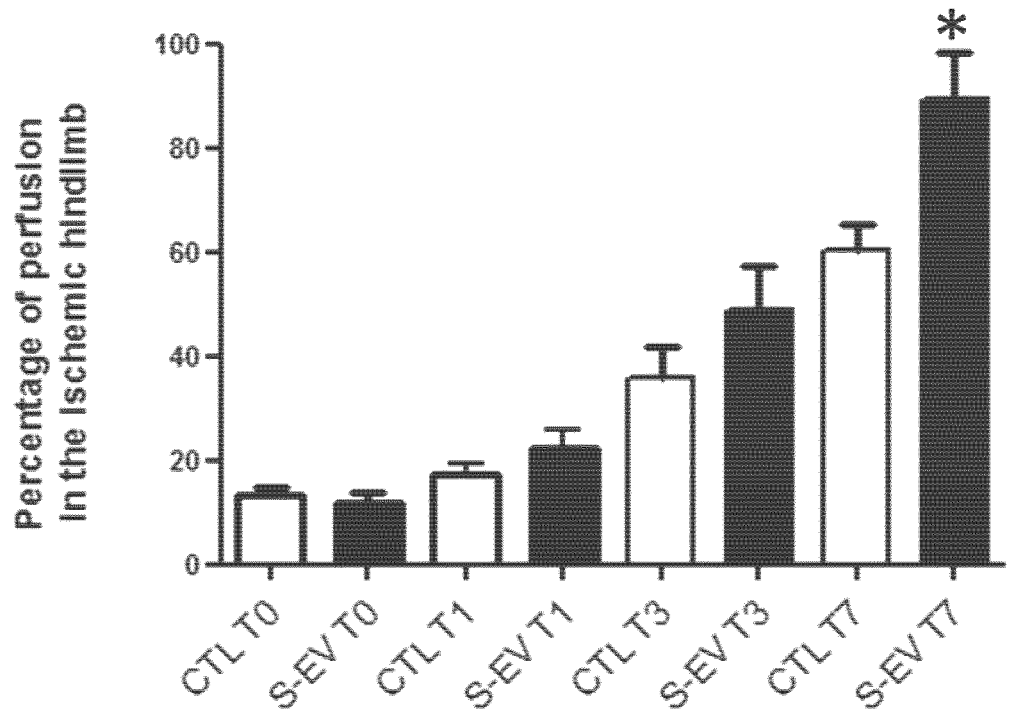

FIG. 5 shows that quantitative analysis of perfusion measured by laser doppler blood flow indicates that EVs derived from serum of healthy subjects (S-EV) significantly enhanced perfusion in ischemic hindlimb compared to controls (CTL) seven days after surgery. Data are expressed as mean±SD; *p value<0.05, (Mann Whitney non-parametric test).

Figure 6:
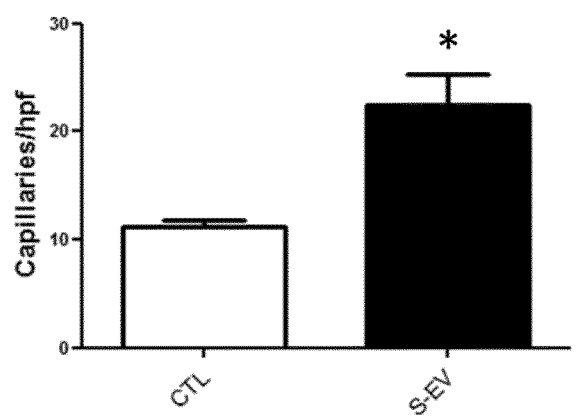

FIG. 6 shows the results of quantitative analysis of capillary density within the gastrocnemius muscles of the ischemic hindlimb seven day after surgery. Immunoflourescence analysis using a anti-CD31 mAb indicates that EVs significantly increased capillary density compared to controls (CTL). Data are expressed as mean±SD; *p value<0.05, (t test).

Figure 7:
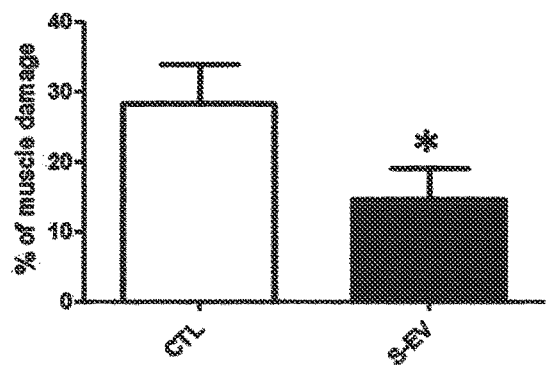

FIG. 7 shows the results of quantitative analysis of areas of muscle damage and of muscle fibers in hematoxilin-eosin stained gastrocnemius muscles from ischemic hindlimbs seven day after surgery. sEVs significantly reduces muscle damage compared to controls (CTL). Data are expressed as mean±SD; *p value<0.05, (t test).

Figure 8:
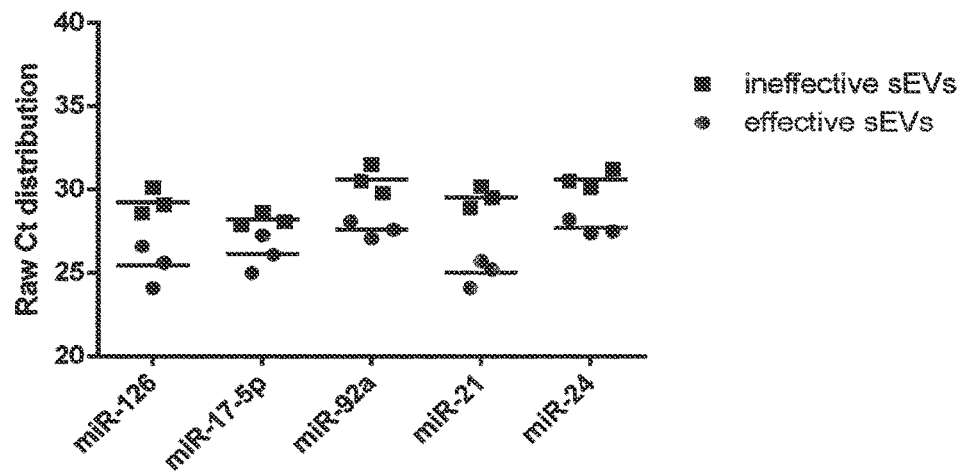

FIG. 8 shows the results of comparative real time PCR analysis. Effective sEVs showed an enrichment in the pro-angiogenic miR-126, miR17-5p, miR-92a, miR-21 and miR-24 (effective sEV vs ineffective sEV, coefficient of variation ranging from 17% for miR-126 to 33% for miR-21).

Figure 9:
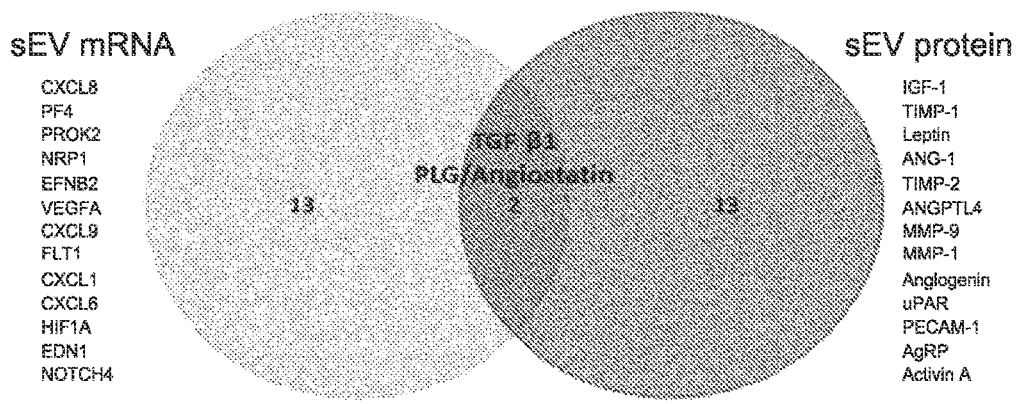

FIG. 9 shows the first 15 angiogenic mRNA and proteins expressed by sEVs identified by mRNA and protein microarray analysis. TGFBeta1 and Angiostatin were commonly detected.

Figure 10:
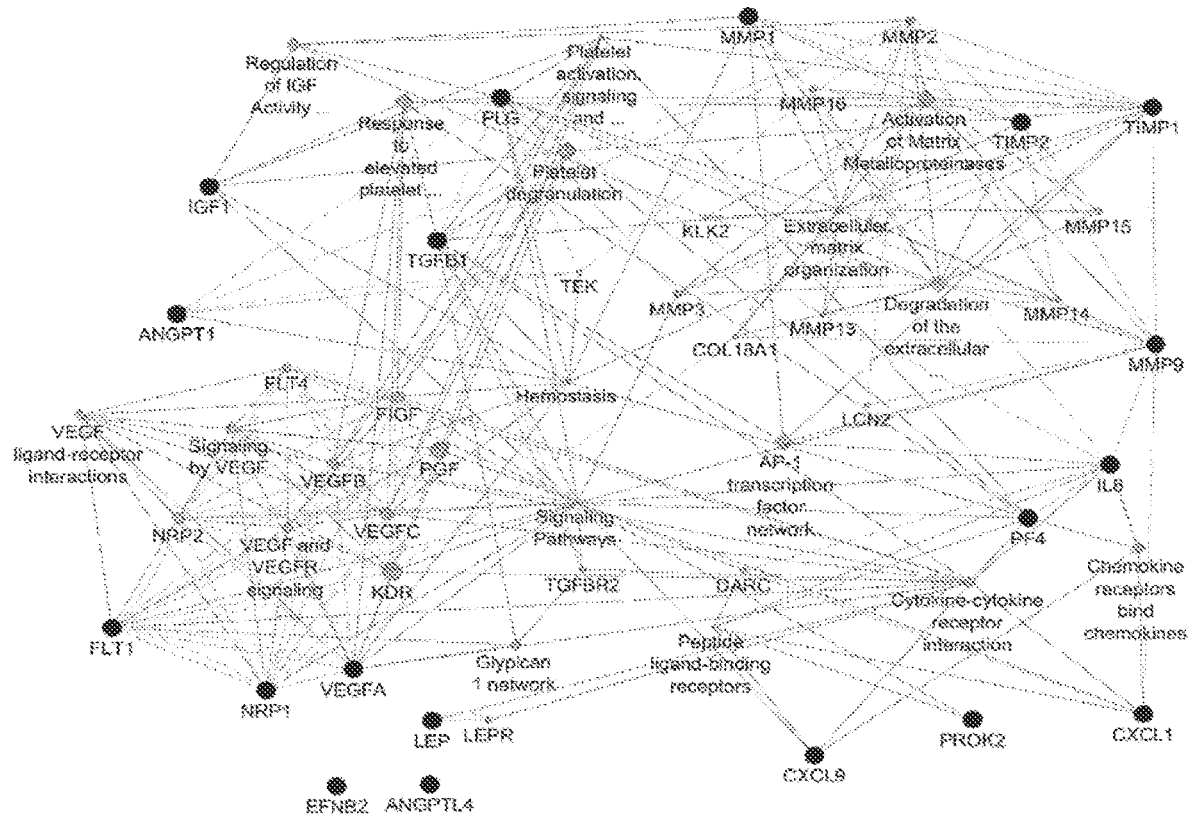

FIG. 10 shows the cross-match between sEV transcripts and proteins, that revealed a significant positive correlation with: cytokine-to-cytokine interaction (enrichment GO score:3.7; p-value: 4.67E-06), positive regulation of blood vessel endothelial migration (enrichment GO score: 3.5; p-value: 3.49E-04), endothelial cell migration (enrichment GO score: 3.1; p-value: 5.03E-05), VEGF signaling pathway (enrichment GO score: 3.1; p-value: 0.01), activation of matrix metalloproteinases and extracellular matrix organization (enrichment GO score: 3.4; p-value: 9.17E-06). Functional annotation enrichment analysis was performed using Funrich software and geMANIA plug in on Cytoscape.

FIGS. 11 and 12 are tables showing that sEVs up-regulated 63 angiogenic-related genes and downregulated 21 genes on ECs (FIG. 11), while VEGF treatment showed an upregulation of 48 genes and downregulation of 36 genes (FIG. 12). Results were represented as fold increase/decrease with respect to control sample.

Figures 13, 14:
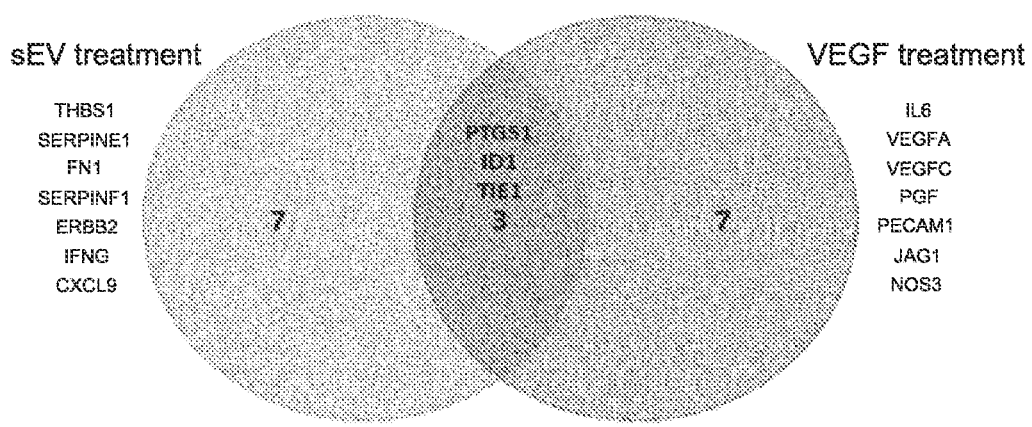

FIG. 13 is a Venn Diagramm representing sEV and VEGF treatment. Up-regulated transcripts with significant fold increase (fold change≥3) with respect to control samples (untreated ECs).

FIG. 14 is a table showing that the GO-based functional analysis revealed an enrichment for genes associated with TGF-beta signalling pathway (P<0.01) in ECs recovered from capillary-like structures formed in response to EVs.

Figure 15:
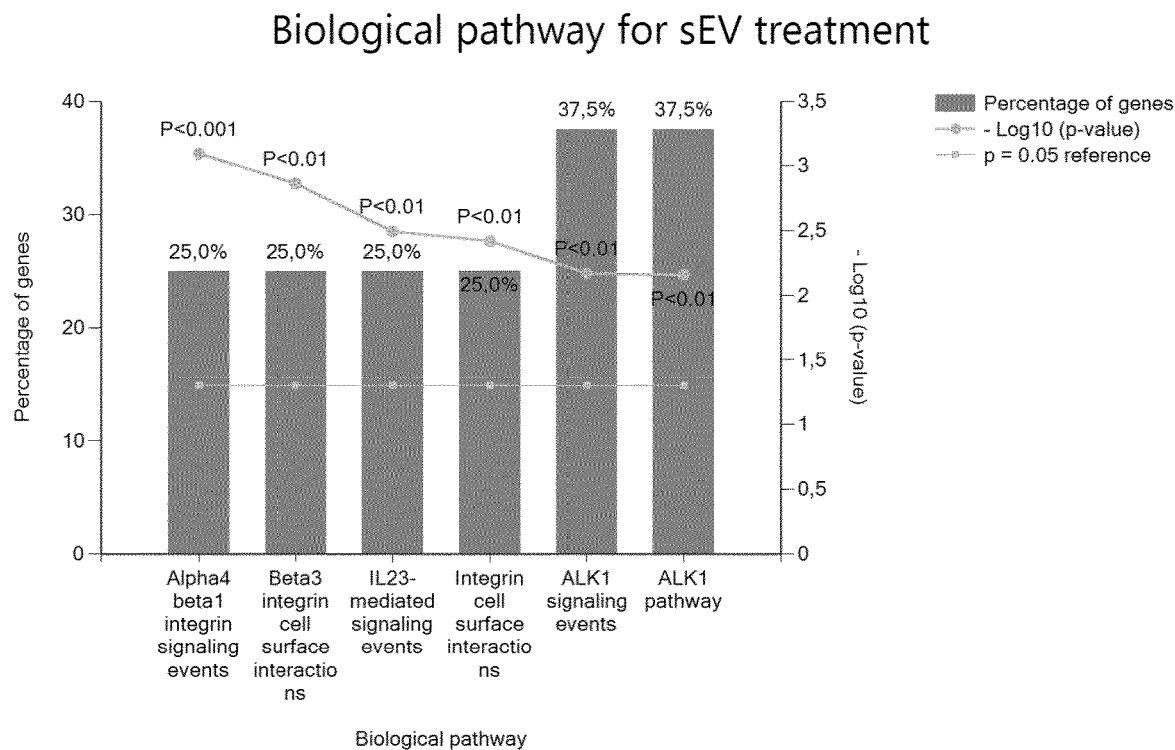

FIG. 15 is a diagram showing that sEV administration correlates with the expression of genes linked to the activation phase of angiogenesis. The most representative clusters of genes consist of genes involved in the ALK1 signaling events and pathway.

Figure 16:
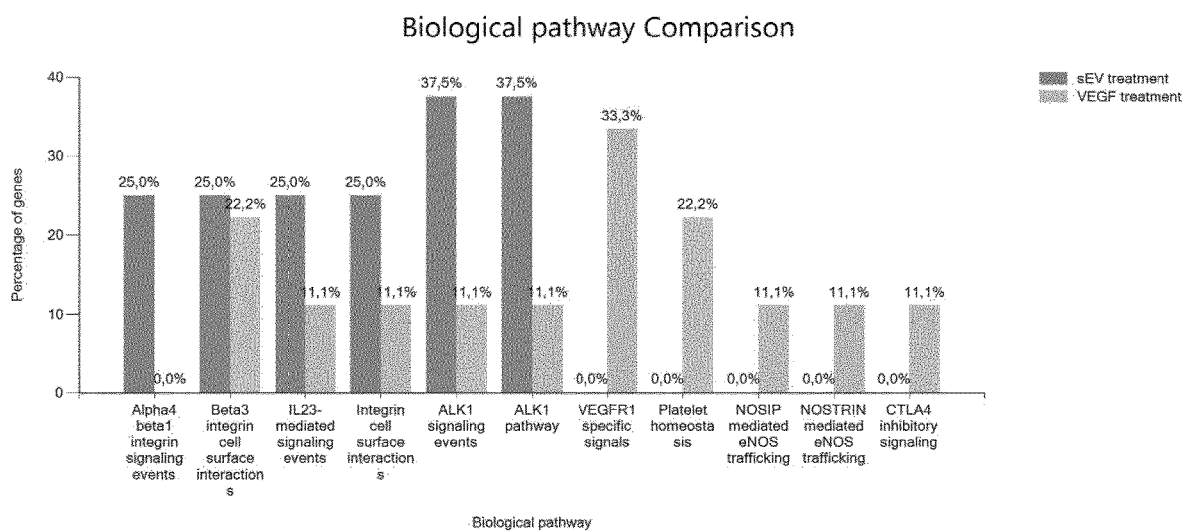

FIG. 16 is a histograph comparing the biological pathway of sEV treatment and VEGF treatment.

The invention is further illustrated by the following examples, which are provided by way of illustration only and are not intended to limit the scope of the invention as defined by the appended claims.

EXAMPLES

1. Methods 1.1. Serum EVs Isolation

Human serum from healthy blood donors (n=18) was provided by the Blood Bank of Citta della Salute e della Scienza di Torino, after informed consent and approval by the internal Review Board of Blood Bank. All human and animal experiments were performed in accordance with the European Guidelines and policies and approved by the Ethical Committee of the University of Turin and by the Italian Institute of Health.

sEVs from each donor were obtained from 110 ml serum bags by centrifuging serum at 3.000 rpm for 20 minutes to remove debris. The supernatant was subsequently ultracentrifuged at 100.000 for 2 h at 4° C. EVs pellets were then re-suspended in a final volume of 1 ml of RPMI with 1% of DMSO and stored at −80° C. sEV were then thawed and used for biological assays and molecular analysis.

1.2. Guava FACS Analysis sEVs FACS analysis was performed with Guava easyCyte™ Flow Cytometer (Millipore, Germany).

sEVs from healthy donors were incubated with antibodies directed to specific markers for monocyte/macrophages (CD14, CD15), leukocytes (CD45), adhesion molecules (alpha6, CD44, CD29), endothelial cells (CD31, KDR) and platelets (CD42b, CD62P, P SEL). FITC or PE mouse nonimmune isotypic IgG (Beckton Dickinson, Franklin Lakes, N.J.) were used as control. sEVs were incubated with specific or control isotype antibody for 1 hour at 4° C. and analyzed by FACS.

1.3. Nanoparticle Tracking Analysis sEVs were analyzed by the Nanosight LM10 system (Nanosight Ltd., Amesbury, UK). Briefly, sEVs preparations were diluted (1:1000) in sterile 0.9% saline solution and analyzed by NanoSight LM10 equipped with the Nanoparticle Analysis System & NTA 1.4 Analytical Software. The number of total EVs for each patient was obtained by multiplying the value given by the instrument (microparticles/ml) for the dilution made for the analysis and for the number of microliters in which sEVs were resuspended.

1.4. sEV Potency Test

In preliminary studies, a dose response curve was performed to evaluate the number of sEVs needed to obtain the best biological response on human microvascular endothelial cells (HMEC). The acronym ECs will be used throughout the study. By using 4 different sEV samples, we found that $5 \times 10^4$ sEVs/target cell was the most effective sEV dose. Thus, $5 \times 10^4$ EVs/target cell were used throughout the in vitro study.

Therefore, sEVs from single samples were evaluated for their pro-angiogenic activity by either BrdU cell proliferation assay or in vitro tubulogenesis assay or both.

To evaluate sEVs potency (expressed in terms of % activity), a negative and positive control were used. In the BrdU assay, the negative control was medium without serum; the positive control was medium with 10% serum. In the in vitro angiogenesis assay, the positive control was medium with 10 ng/ml VEGF, the negative control was medium without added VEGF).

The following formula was applied:

$$\% \text{ activity} = \frac{\text{composition value} - \text{negative control value}}{\text{positive } crtl \text{ value} - \text{negative control value}} \times 100.$$

Values exceeding 50% of the VEGF pro-angiogenic capability (i.e. the positive control) were considered as efficient sEVs.

Pools of sEVs were obtained by combining 2 different sEV samples (1:1). Pooled sEVs were also evaluated by BrdU cell proliferation assay and in vitro angiogenesis assays.

A detailed description of the BrdU cell proliferation assay and in vitro angiogenesis assays carried out is provided herein below.

1.4.1 BrdU Cell Proliferation Assay

HMEC cells (ATCC CRL 3243) were seeded in 96 well (3000 cell per well) in 300 ul of EBM (LONZA) +10% FBS medium. After 24 hours, HMEC cells were starved with DMEM without FBS for 3 hours and then stimulated with $30 \times 10^6$ EVs per well (10000 EVs per target cell) resuspended in DMEM without FBS. For negative and positive controls DMEM without FBS and DMEM+10% FBS were used. After 4 hours of EV stimulation, 10 ul of BrdU was added to each well (BrdU final concentration 10 µM) and HMEC cells were incubated for 18 h.

After stimulation and BrdU incubation, BrdU labelling was detected by BrdU labelling and detection kit (ROCHE). Briefly, 96 well plate was washed 3 times with 250 ul RPMI+10% FBS and cells were fixed by 200 ul precooled fixative (Ethanol 70% HCl 0.5M) for 30 min at −20° C. and then re-washed 3 times with 250 ul RPMI+10% FBS. Plate was incubated with 100 ul nuclease solution for 30 min at 37° C., washed 3 times with 250 ul RPMI+10% FBS and then incubated with 100 ul anti-BrdU-POD Fab fragment for 30 min at 37° C. Plate was filled with 100 ul peroxidase substrate at room temperature for 2-30 min and plate was read in a microtiter plate reader at 405 nm with a reference wavelength at 490 nm.

In order to calculate the % of effect, O.D. derived from EV stimulated samples were elaborate as follow:

The O.D. of negative control (DMEM without FBS) was set as 0% of effect and the O.D. of positive control (DMEM+ 10% FBS) was set as 100% of effect. The O.D. of the EV-stimulated samples was converted in % of effect by the following formula:

(sample O.D.−negative control O.D.)/(positive control O.D.−negative control O.D.)*100

1.4.2 In Vitro Tubulogenesis Assay 24 well plate was coated with a thin layer of growth factor reduced matrigel and left 1 hour at 37° C. HUVEC cells (ATCC CRL 1730) were seeded in matrigel coated wells (25000 cells per well) with $1.25 \times 10^9$ EVs per well (50000 EVs per target cell) re-suspended in 500 ul EBM (endothelial basal medium) (LONZA) without FBS. For negative and positive controls, EBM without FBS and EBM without FBS+10 ng/ml hVEGF (Abcam) were used. After 24 hours, 5 micrographs for each well were taken, the capillary-like structures were counted by ImageJ software and the mean count of capillary-like structures per field for each EV sample was calculated.

In order to calculate the % of effect, the mean count of capillary-like structures were elaborate as follow:

The capillary-like structure count (CLSC) of negative control (EBM without FBS) was set as 0% and the CLSC of control positive (EBM without FBS+10 ng/ml VEGF) was set as 100%. The CLSC of the samples was converted in % of effect by the following formula:

(sample CLSC−negative control CLSC)/(positive control CLSC−negative control CLSC)×100.

The sEVs potency was calculated by the arithmetic mean of BrdU and in vitro tubulogenesis test percentage of effect expressed in terms of overall effect percentage.

1.5 Animal Studies

Animal studies were conducted in accordance with the National Institute of Health Guide for the Care and Use of Laboratory Animals. Angiogenesis was assessed by measuring the growth of blood vessels from subcutaneous tissue into a solid gel of basement membrane, as previously described (Lopatina T, Bruno S, Tetta C, Kalinina N, Porta M, Camussi G. Platelet-derived growth factor regulates the secretion of extracellular vesicles by adipose mesenchymal stem cells and enhances their angiogenic potential. *Cell Commun Signal.* 2014; 12(1): 26. doi: 10.1186/1478-811X-12-26). First, ECs ($1 \times 10^6$ cells/injection) were incubated overnight with sEVs ($5 \times 10^{10}$ EVs per $1 \times 10^6$ of ECs). Then, male severe combined immunodeficiency (SCID) mice (6 weeks old) were injected subcutaneously with 0.5 ml of ice-cold BD Matrigel Matrix Growth Factor Reduced (BD Biosciences, Franklin Lakes, N.J.), which had been mixed with pre-stimulated ECs. Equal number of non-stimulated ECs was used as a negative control. The Matrigel plugs were excised 10 days after and fixed in 4% paraformaldehyde for 4 h. Matrigel-containing paraffin sections (5-8 μm thick) were stained by trichrome stain method. The vessel lumen area was determined as previously described (Lopatina T, Bruno S, Tetta C, Kalinina N, Porta M, Camussi G. Platelet-derived growth factor regulates the secretion of extracellular vesicles by adipose mesenchymal stem cells and enhances their angiogenic potential. Cell Commun Signal. 2014; 12(1): 26. doi: 10.1186/1478-811X-12-26).

1.5.1 Murine Model of Hind Limb Ischemia

SCID mice (Charles River Laboratories), age 7 to 8 weeks and weighing 18 to 22 g, were anesthetized with i.m. injection of zolazepam 80 mg/Kg. Postoperatively, the animals were closely monitored, and analgesia with Ketorolac (5 mg/Kg) was administered if required.

Under sterile conditions, a small skin incision were made overlying the middle portion of the left hind limb of each mouse. The proximal end of the left femoral artery and the distal portion of the saphenous artery were ligated, dissected and excised. The overlying skin was closed using a sterilized 6-0 silk suture. In preliminary experiments, different sEV number and sEV administration routes were evaluated. The latter included intravenous (iv) or intramuscular (i.m.) alone or differently combined. We found that the best administration rout in term of animal distress and response to treatment was: T0 ($1 \times 10^{10}$ iv), T1 and T2 ($0.5 \times 10^{10}$ i.m.). Animals were sacrificed at day 7 for histological analysis.

1.5.2 Monitoring of Hind Limb Blood Flow

After anesthesia, hair was removed from both legs using a depilatory cream, following which the mice were placed on a heating plate at 37° C. for 3 minutes to minimize temperature variations. Hind limb blood flow was measured using a Laser Doppler Blood Flow (LDBF) analyzer (PeriScan PIM 3 System, Perimed, Stockholm, Sweden). Immediately before surgery, and at day 0, 3, 7 after surgery LDBF analysis was performed on hind limbs and feet. Blood flow was displayed as changes in the laser frequency using different color pixels. After scanning, stored images were analyzed to quantify blood flow. To avoid data variations caused by ambient light and temperature, hind limb blood flow was expressed as the ratio of left (ischemic) to right (non-ischemic) LDBF.

1.5.3 Evaluation of Capillary Density

Capillary density within gastrocnemius muscles was quantified by immunofluorescence analysis. Muscle samples were embedded in OCT compound (Miles) and snap-frozen in liquid nitrogen. Tissue slices (5 μm in thickness) were prepared and capillary endothelial cells were identified by immunofluorescence using a monoclonal antibody against mouse CD31 (Santa Cruz Biotechnology Inc., Santa Cruz, Calif.). Fifteen randomly chosen microscopic fields from three different sections in each tissue block were examined for the count of capillary endothelial cells for each mouse specimen. Capillary density was expressed as the number of CD-31-positive features per high power field (×400).

1.5.4 Histology

The gastrocnemius muscle from ischemic and non-ischemic limb was removed at day 7 after surgery, immediately fixed with 4% paraformaldehyde for 8 hours and then embedded in paraffin. Tissue slices were stained with hematoxylin and eosin. Slides were examined under light microscopy at ×200 magnification. Images were acquired from all the injured area of the ischemic limb sections for the count of the total muscle fibers and of the fibers with small-diameter and with multiple central nuclei that are indicative of the regeneration process. Random images from the total non-ischemic limb section were considered as a control.

1.6 Protein Array

Proteins from different sEVs were extracted with NP40 lysis buffer (150 mM NaCl, 50 mM TRIS-HCl pH 8, 1% NP40). Angiogenic protein profile was performed using Quantibody® Human Angiogenesis array 1000 (Ray Biotech) which contain a combination of two non-overlapping array to quantitatively measure the expression of 60 human angiogenic proteins. 25 μg of protein were loaded for each sample. Data were subjected to background subtraction and protein concentration was obtained from the different standard curve of the array. Functional annotation enrichment analysis was performed using Funrich software and geMANIA plug in on Cytoscape.

1.7 mRNA-Angiogenic Microarray Profile sEVs total RNA was isolated using All in One (Norgen, Thorold, ON, Canada) extraction method. RNA concentration and purity were detected by the NanoDrop1000 spectrophotometer. The samples of absorbance at 260-280 nm between 1.8 and 2.0 were adopted.

cDNA was synthesized by $RT^2$ First Strand kit (SABiosciences) following the manufacturer's instructions. Gene expression profiling using the Angiogenesis $RT^2$ Profiler PCR Array (PAHS 024, SA Biosciences) was performed by loading 200 ng of cDNA for each sEV sample. The expression profile of 84 key genes in angiogenesis was analyzed (list of genes available on website: http://www.sabiosciences.com). Quantitative reverse transcriptase PCR (RT-PCR) was performed using the StepOne Plus™ System (AB Applied Biosciences). Relative gene expression was determined using the $\Delta\Delta C_T$ method. Angiogenesis $RT^2$ Profiler PCR Array was also performed on tubule-like structures formed upon sEV administration. ECs were harvested and purified with the RNeasy Mini kit (Qiagen, GmbH, Germany), then retro transcribed to cDNA and processed using the Angiogenesis $RT^2$ Profiler PCR Array. Five endogenous control genes: beta-2-microglobulin (B2M), hypoxanthine phosphoribosyl transferase (HPRT1), 60S acidic ribosomal protein P0 (RPLP0), glyceraldehyde-3-phosphate dehydrogenase (GAPDH), and b-actin (ACTB) present on the PCR array were used for normalization. The fold-change for each treated sample relative to the control sample corresponded to $2^{-\Delta\Delta Ct}$. Changes in gene expression between treated and untreated ECs were illustrated as a fold increase/decrease. Data were further analyzed using the Expression Suite and the Funrich Software.

2. Results

2.1 Characterization of sEVs

Surface antigens of different cell populations (platelets, endothelial, monocyte, leukocyte and adhesion molecule markers) were examined in sEVs by Guava FACS analysis. The analysis showed that EVs from serum were a heterogeneous collection coming from different blood cell populations (FIG. 1).

Figure 2A:
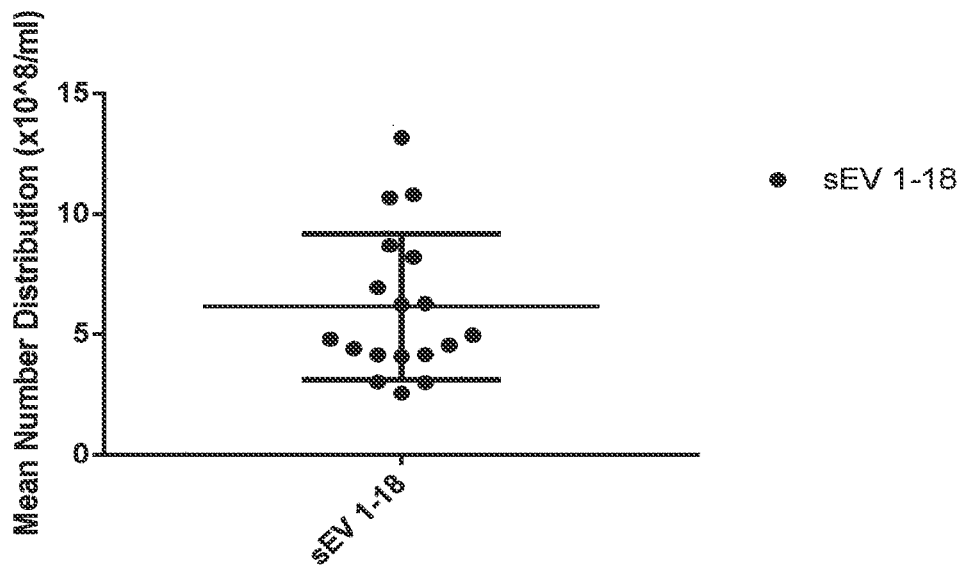
Figure 2B:
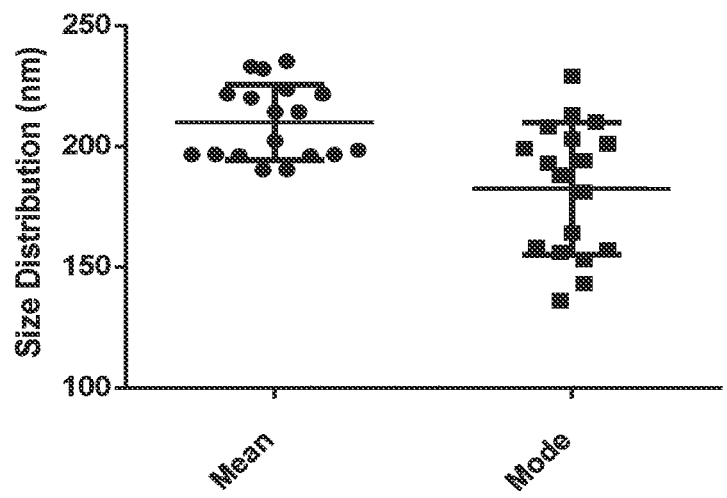
Figures 2C, 3:
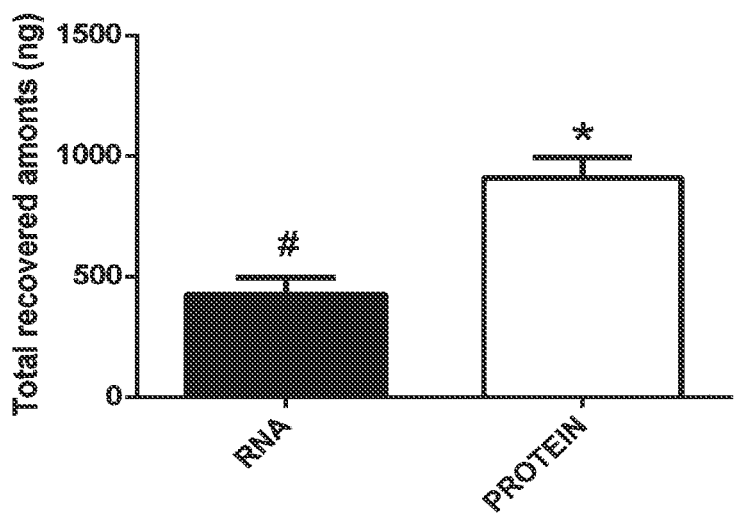
FIG. 3 is a table showing the pro-angiogenic activity of EVs from single serum, as analyzed by BrdU and in vitro tubulogenesis assays. 14 out of 18 sEV samples showed values exceeding the 50% of VEGF activity.

By Nanosight analysis, we did not notice significant differences in sEV number and size among different healthy donors. sEV mean particle concentration recovered from a bag of 110 ml was around $6.16 \times 10^8$ particles/ml (FIG. 2A) and sEV diameters was approximately 210 nm with a modal particle size of 183 nm (FIG. 2B). Starting from $2 \times 10^{11}$ of total particles, sEV RNA and protein recovery was similar in all samples analyzed (n=18) ranging from 300 to 500 ng (RNA) and about 1 μg (proteins) (FIG. 2C).

To select sEV with proangiogenic activity, a "test of potency" using as internal control VEGF was performed. Efficient sEVs were considered those demonstrating almost 50% of VEGF proangiogenic effects when analyzed for their ability to induce EC proliferation and tube-like structure formation. As shown in FIG. 3, 14 out of 18 sEV samples showed values exceeding the 50% of VEGF activity. To further validate these results selected sEVs sharing comparative pro-angiogenic activities were pooled and analyzed for their biological activities. Of note, we demonstrated that these pooled sEVs showed a comparable biological effects with respect to the distinct sEV preparation (FIG. 4A). This indicates that sEVs biological activity was not lost even when pooled.

2.2 sEVs Induce In Vivo Angiogenesis

In order to confirm our potency test, in vivo experiments were performed by using an in vivo SCID mouse model. To this purpose ECs were treated with sEVs ($5 \times 10^4$ sEV/cell), mixed with Matrigel and injected subcutaneously into SCID mice. After one week, wheals were removed and analyzed. As shown in FIG. 4B, sEVs display proangiogenic activities even when analyzed in vivo. Similar effects were detected when pooled sEVs were analyzed (FIG. 4B).

2.3 sEVs Improve Reperfusion Recovery in a Mouse Model of PAD

The angiogenetic effect of sEVs was evaluated in a murine model of ischemic hind limb that mimics PAD in humans. A total amount of $2 \times 10^{10}$ sEVs was administrated daily after surgery ($1 \times 10^{10}$ immediately after intervention (T0), $0.5 \times 10^{10}$ at day one (T1) and at day two (T2)). To evaluate whether different ways of administration could impact on the angiogenetic effects, sEVs were administered i) intravenously in the tail vein at T0, T1 and T2 (data not shown); ii) intramuscular directly in the ischemic hind limb at T1, T1 and T2 (data not shown) and iii) intravenously at T0 and intramuscular at T1 and T2. The intravenously administration of sEVs immediately after intervention and the subsequent intramuscular administration proved to lead the best response. Blood perfusion in the ischemic hind limb was evaluated using a Laser Doppler Perfusion imaging. Immediately after surgery, the ratio between the ischemic and non-ischemic hind limb decreased to 0.13±0.06 in CTL group and 0.12±0.04 in sEVs group (n=10/group). In the sEVs-treated group hind limb perfusion ratio significantly increased at day 7 after surgery compared with the CTL group (0.89±0.26 vs 0.6±0.18, p<0.05) (FIG. 5). Consistently, capillary density in the ischemic hind limbs was significantly increased in sEVs-treated mice compared to the control group (22.4±5.5 vs 11.2±1.8, p<0.05) (FIG. 6).

Analysis of tissue damage (gastrocnemius muscles) revealed that muscles from sEVs-treated mice contained a reduced area of muscle damage (FIG. 7) and an increased vascular density. Thus, in our model, sEVs appear to protect against ischemia-induced damage.

2.4 sEV-Cargo Analysis

The above results led us to investigate the contribute of angiogenic-related miRs, mRNAs and proteins carried by sEVs in mediating such functional effects. To this purpose, first, miRs known to be involved in neovascularisation (Caporali A, Emanueli C. MicroRNAs in postischemic vascular repair. Cardiol Res Pract. 2012; 1(1). doi: 10.1155/2012/486702) were evaluated.

Real time PCR analysis reported in FIG. 8 demonstrates that, compared to ineffective sEVs, effective sEVs showed a significant enrichment of the well-known pro-angiogenic miRs; miR-126, miR17-5p, miR-92a, miR-21 and miR-24 (effective sEV vs ineffective sEV coefficient of variation CV ranging from 17% for miR-126 to 33% for the miR-21).

By mRNA and protein microarray analysis we selected the first 15 angiogenic mRNA and proteins expressed by sEV (FIG. 9). We observed that TGFb1 and Angiostatin were commonly detected in mRNA and proteins (TGFb1: mRNA mean Ct value of 28.8 and protein quantification: 6.3 ng/ml, Angiostatin: mRNA mean Ct value: 28.2 and protein quantification: 11.5 ng/ml).

The cross-match between sEV transcripts and proteins revealed a significant positive correlation with: activation of matrix metalloproteinases and extracellular matrix organization (enrichment GO score: 3.4; p-value: 9.17E-06), cytokine-to-cytokine interaction (enrichment GO score: 3.7; p-value: 4.67E-06), endothelial cell migration (enrichment GO score: 3.1; p-value: 5.03E-05), positive regulation of blood vessel endothelial migration (enrichment GO score: 3.5; p-value: 3.49E-04), VEGF signaling pathway (enrichment GO score: 3.1; p-value: 0.01) (FIG. 10).

2.5 Gene Pattern Modulation Upon In Vitro sEV Treatment

To validate the biological relevance of sEVs cargo in inducing proangiogenic cues, mRNA-angiogenesis microarrays were analyzed on ECs recovered from capillary-like structures formed in response to sEVs, or VEGF (positive control) and compared to untreated ECs (internal control).

Although the pro-angiogenic effects exerted by sEVs and VEGF was almost comparable, a different pattern of gene expression was detected: upon sEV treatment (4 samples were analyzed) 63 angiogenic-related genes were found up-regulated while 21 genes down-regulated (FIGS. 11-12); upon VEGF treatment 48 genes were upregulated and 36 genes were down-regulated (FIG. 12). For each treatment, the up-regulated transcripts with a fold increase ≥3 with respect to control samples (untreated ECs) were used for further investigation. On this basis we selected the following 10 highest expressed genes. For sEVs treatment: PTGS1, ID1, THBS1, SERPINE1, FN1, SERPINF1, ERBB2, TIE1, IFNG, and CXCL9; for VEGF treatment: IL6, VEGFA, VEGFC, PTGS1, PGF, TIE1, PECAM1, ID1, JAG1, and NOS3 (FIG. 13). The Venn diagram reported in FIG. 13 also shows that PTGS1, ID1 and TIE1 genes were shared by both treatments.

To dissect the molecular events associated with sEV treatment, different Gene ontology (GO) database were interrogated. GO-based functional analysis revealed an enrichment for genes associated with TGFb1 signalling pathway (P<0.001) (FIG. 14) in ECs recovered from capillary-like structures formed in response to sEVs. Of note, a deeper GO analysis revealed that sEV administration correlate with the expression of genes linked to the activation phase of angiogenesis TGFb/ALK1-mediated (FIG. 15). As a matter of fact, the most representative clusters of genes consisted of genes involved in the ALK1 signaling events and pathways (FIG. 15). These latter results further substantiate the transcriptomic analysis which identified ID1 (FIG. 11 or FIG. 13) as one of the highest expressed genes. FIG. 16, which illustrates the comparison between sEVs- and VEGF-mediated biological pathways, adds further support in recognizing the ALK1 cascade as the most relevant sEV mechanism of action.

The invention claimed is:

1. A method of manufacturing a pharmaceutical preparation of extracellular vesicles (EVs), comprising the steps of:
    isolating EVs from multiple preparations of a body fluid or from the conditioned medium of a cell culture;
    preparing one or more samples from the isolated EVs at a predetermined concentration of EVs;
    testing the activity of each EVs sample in a potency test, wherein the potency test is one or both of a tubulogenesis assay and a BrdU cell proliferation assay;
    selecting for further processing to a pharmaceutical preparation the samples which exceed a predetermined activity; and
    pooling two or more of the active EVs samples.

2. The method according to claim 1, wherein the potency test is the tubulogenesis assay and comprises the following steps:
    measuring the activity of the composition by a tubulogenesis assay;
    measuring the activity of a negative control by a tubulogenesis assay;
    measuring the activity of a positive control by a tubulogenesis assay; and
    calculating the % activity of the composition in the tubulogenesis assay by applying the following formula:

$$\% \text{ activity} = \frac{\text{composition value} - \text{negative control value}}{\text{positive } crtl \text{ value} - \text{negative control value}} \times 100.$$

3. The method of claim 1, wherein the EVs are from human cells.

4. The method according to claim 1, wherein the potency test is the BrdU cell proliferation assay and comprises the following steps:
    measuring the activity of the composition by a BrdU cell proliferation assay;
    measuring the activity of a negative control by a BrdU cell proliferation assay;
    measuring the activity of a positive control by a BrdU cell proliferation assay; and
    calculating the % activity of the composition in the BrdU cell proliferation assay by applying the following formula:

$$\% \text{ activity} = \frac{\text{composition value} - \text{negative control value}}{\text{positive } crtl \text{ value} - \text{negative control value}} \times 100.$$

5. The method according to claim 1, wherein the potency test is both the tubulogenesis assay and the BrdU cell proliferation assay.

* * * * *

UNITED STATES PATENT AND TRADEMARK OFFICE
CERTIFICATE OF CORRECTION

PATENT NO. : 11,464,799 B2
APPLICATION NO. : 16/341319
DATED : October 11, 2022
INVENTOR(S) : Maria Felice Brizzi et al.

It is certified that error appears in the above-identified patent and that said Letters Patent is hereby corrected as shown below:

On the Title Page

Item (73), Assignee: Please change "USICYTE EV AG" TO --UNICYTE EV AG--.

Signed and Sealed this
Tenth Day of January, 2023

Katherine Kelly Vidal
*Director of the United States Patent and Trademark Office*